United States Patent [19]

McGeer et al.

[11] Patent Number: 5,192,753
[45] Date of Patent: Mar. 9, 1993

[54] ANTI-RHEUMATOID ARTHRITIC DRUGS IN THE TREATMENT OF DEMENTIA

[76] Inventors: Patrick L. McGeer, 4727 West 2nd Ave., Vancouver, B. C., Canada, V6T 1C1; Joseph Rogers, 7646 W. Julie Dr., Glendale, Ariz. 85308; John Sibley, 87 Leddy Crescent, Saskatoon, Saskatchewan, Canada, S7H 3Y9; Edith McGeer, 4727 West 2nd Ave., Vancouver, B. C., Canada, V6T 1C1

[21] Appl. No.: 689,499

[22] Filed: Apr. 23, 1991

[51] Int. Cl.⁵ ................ A61K 31/60; A61K 31/615; A61K 31/54; A61K 31/44; A61K 31/425; A61K 31/42; A61K 31/415; A61K 31/40; A61K 31/38; A61K 31/195; A61K 31/19

[52] U.S. Cl. .................... 514/159; 514/162; 514/165; 514/226.5; 514/356; 514/365; 514/375; 514/404; 514/419; 514/420; 514/423; 514/428; 514/429; 514/448; 514/567; 514/569; 514/570

[58] Field of Search ............ 514/165, 570, 549, 552, 514/560, 878, 879, 159, 162, 226.5, 356, 375, 404, 419, 420, 423, 428, 429, 448, 567, 569

[56] References Cited

FOREIGN PATENT DOCUMENTS 61-106520 5/1986 Japan .

OTHER PUBLICATIONS

*Martindale, The Extra Pharmacopoeia*, 28th Ed. (1982) pp. 234-282.

W. N. Kelley, E. D. Harris, Jr., S. Ruddy, and C. B. Sledge, "The Textbook of Rheumatology", 1989 W. B. Saunders Company.

D. A. Evans, H. H. Funkenstein, and M. S. Albert et al. "Prevalence of Alzheimer disease in a community population of older Persons", JAMA 1989; 262: 2551-2556.

J. A. Mortimer, "Alzheimer's Disease and Senile Dementia: Prevalance and Incidence", In: B. Reisberg (ed) Alzheimer's Disease, The Free Press, 1983, 141-148.

R. Sulkava, J. Wikstrom, A. Aromaa et al., "Prevalence of Severe Dementia in Finland", Neurology 1985; 35: 1025-1029.

S. Itagaki, P. L. McGeer, H. Akiyama, "Presence of T-cytotoxic Suppressor and Leucocyte Common Antigen Positive Cells in Alzheimer's Disease Brain Tissue", Neuroscience Letters 1988; 91: 259-264.

J. Rogers, J. Luber-Narod, S. D. Styren, and W. H. Civin, "Expression of Immune System-Associated Antigens By Cells of the Human Central Nervous System: Relationship to the Pathology of Alzheimer's Disease" Neurobiology of Aging, 1988, vol. 9. 339-349.

P. L. McGeer, H. Akiyama, S. Itagaki, and E. G. McGeer, "Immune System Response in Alzheimer's Disease", The Canadian Journal of Neurological Sciences 1989; 16: 516-527.

P. L. McGeer, H. Akiyama, S. Itagaki and E. G. McGeer, "Activation of the Classical Complement Pathway in Brain Tissue of Alzheimer Patients", Neuroscience Letters 1989; 107: 341-346.

P. L. McGeer, E. G. McGeer, J. Rogers and J. Sibley, "Anti-inflammatory Drugs and Alzheimer Disease", The Lancet 1990; 335: 1037.

*Primary Examiner*—Frederick E. Waddell
*Assistant Examiner*—Raymond J. Henley, III
*Attorney, Agent, or Firm*—Barrigar & Oyen

[57] ABSTRACT

This invention pertains to the novel use of anti-rheumatoid arthritic drugs in the treatment of dementia. A method of treating dementia in human beings which comprises administering to the human being a therapeutic amount of a non-steroidal anti-inflammatory drug (NSAID) which has the ability to inhibit prostaglandin synthesis in the human being.

6 Claims, 2 Drawing Sheets

ANTI-RHEUMATOID ARTHRITIC DRUGS IN THE TREATMENT OF DEMENTIA

FIELD OF THE INVENTION

This invention pertains to the novel use of non-steroidal anti-inflammatory drugs in the treatment of dementia (Alzheimer disease) in human beings.

BACKGROUND OF THE INVENTION

Non-steroidal anti-inflammatory drugs (NSAIDs) are the drugs of choice for the treatment of rheumatoid arthritis (Textbook of Rheumatology, eds. Kelley, W. N., Harris, E. D. Jr., Ruddy, S., Sledge, C. B., Saunders Co., 1989). They have fewer side effects than other classes of anti-arthritic drugs and are therefore almost universally prescribed for this condition. They are characterized by their ability to inhibit prostaglandin synthesis through anti-cyclooxygenase activity. They can be classified chemically as derivatives of arylcarboxylic acids, including salicylic and anthranilic acid derivatives; arylalkanoic acids, including arylacetic, arylpropionic, heteroarylacetic, indoleacetic and indeneacetic acids; and enolic acids, including pyrazolidinediones and oxicams.

While drugs in this class are among the most widely used in medicine, there is no literature or teaching in the art to indicate that any NSAID has been used in the treatment of Alzheimer's disease (dementia). This brain disorder is estimated to affect 0.5-1% of the general population in industrialized countries and threatens to become more prevalent as the average age of the human population increases.

SUMMARY OF THE INVENTION

We have determined that patients with rheumatoid arthritis, most of whom will have been treated with one or more of these agents, have a much lower prevalence of Alzheimer disease than the age-matched general population. We have also determined in a 6 month pilot trial, that Alzheimer cases given indomethacin, a widely used NSAID, showed little or no mental deterioration. NSAIDs are relatively safe agents. While they all have side effects, such side effects are well known due to their very extensive use in a wide range of inflammatory diseases where long term treatment is common.

The invention pertains to a method of treating dementia in human beings which comprises administering to the human being a therapeutic amount of a substance selected from the non-steroidal anti-inflammatory group of cyclooxygenase inhibitors.

The invention also pertains to a composition for treating dementia in human beings which composition comprises a substance or substances selected from the group consisting of non-steroidal anti-inflammatory cyclooxygenase inhibitors, therapeutically acceptable salts thereof, and therapeutically acceptable carriers.

Within the terms of the invention, the NSAIDs include, but are not restricted to, the following chemical agents that inhibit prostaglandin synthesis primarily by their activity against the enzyme cyclooxygenase:

(1) Arylcarboxylic acids: salicylic acid, acetylsalicylic acid, diflunisal, choline magnesium trisalicylate, salicylate, benorylate, flufenamic acid, mefenamic acid, meclofenamic acid, niflumic acid;

(2) Arylalkanoic acids: diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac;

(3) Enolic acids: phenylbutazone, oxyphenbutazone, azapropazone, feprazone, piroxicam, isoxicam, sudoxicam.

The dosage of each agent will vary. For each patient, it will be the dosage that is required to inhibit effectively prostaglandin synthesis in vivo, but not to induce unwanted side effects such as gastrointestinal bleeding. Daily doses of an agent can range from 10 mg to 3 g per 100 kg body weight.

The composition can comprise a NSAID cyclooxygenase inhibitor and a therapeutically acceptable carrier. The substance can be present in the composition at a dosage of 5 mg to 1 gm.

DRAWINGS

DETAILED DESCRIPTION OF A PREFERRED EMBODIMENT OF THE INVENTION

Figure 1:
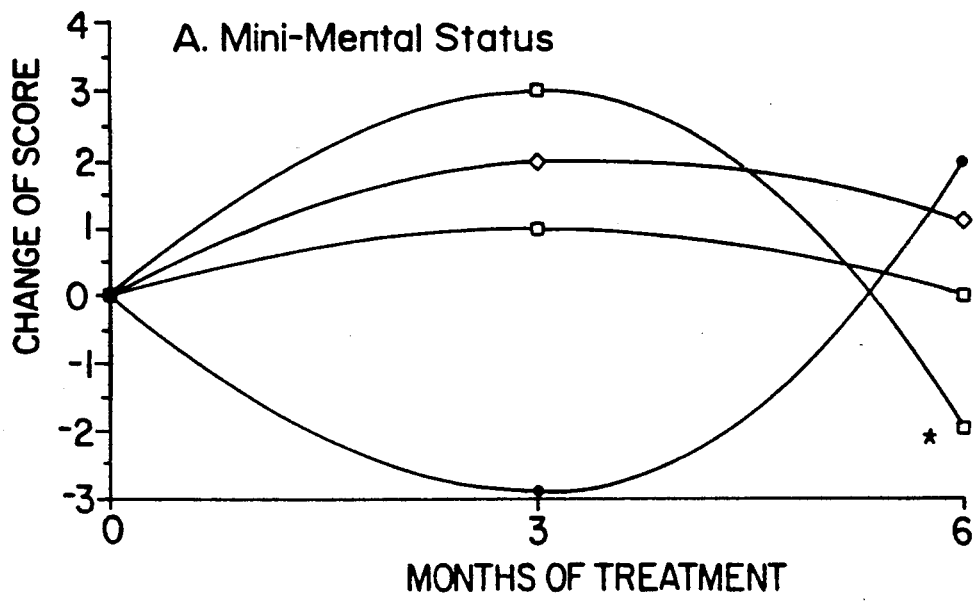
FIG. 1 illustrates a graphical depiction of Mini-Mental Status test results plotted by change of score against months of treatment.

We have conducted research which has demonstrated that changes characteristic of an inflammatory process occur in Alzheimer brain tissue. The cellular and protein alterations that we have observed are similar to those seen in other tissues of the body in diseases where there is an autoimmune disorder, or a persistent, non-lethal pathogen. Rheumatoid arthritis is typical of such diseases. Such diseases respond to a variety of anti-inflammatory agents, which have in common the ability to inhibit cells which attack the human body's own tissues. Based on this research and not wishing to be adversely bound by any theories, we have reasoned that rheumatoid arthritics, who require long term treatment with such agents to keep immune system cells from attacking the joint tissue, would be spared from Alzheimer's disease because such immune system cells would be similarly inhibited from attacking their brain tissue. We have further reasoned that Alzheimer disease can be effectively treated with any drug of the NSAID class since drugs of this class are almost universally prescribed at some stage in rheumatoid arthritis.

We have conducted a survey of patients suffering from rheumatoid arthritis to determine the prevalence of Alzheimer disease in such patients. We have found that the prevalence is dramatically lower than the prevalence of dementia in the age-matched general population. The prevalence of Alzheimer disease in the age group 65 years and over in North America is reported to be from 2.5 to 10.3%, depending on the survey (Evans, D. A., Funkenstein, H. H., Albert, M. S. et al. Prevalence of Alzheimer Disease in a community population of older persons. JAMA 1989; 262: 2551-2556; Mortimer, J. A. Alzheimer's Disease and dementia:

prevalence and incidence. In: Reisberg, B. (ed.) Alzheimer's Disease, Glencoe, Free Press, 1983; Sulkava, R., Wikstrom, J., Aromaa, A. et al. Prevalence of severe dementia in Finland. Neurology 1985; 35: 1025-1029). We have found unexpectedly that the prevalence of Alzheimer disease amongst rheumatoid arthritics 65 years or over is only 0.39% (29/7,490). This is roughly 6 to 26 fold lower in level of prevalence. It is not possible to relate this reduction to any single anti-arthritic drug since patients suffering from rheumatoid arthritis are typically treated with one or more of a variety of anti-inflammatory drugs, with the dose being titrated to produce the best control for each person. However, almost all will have been treated at some stage of their disease with one or more NSAIDs.

Immunohistochemical evidence points to a chronic inflammatory state of the brain in Alzheimer dementia (AD). T4 and T8 lymphocytes and reactive microglia strongly expressing major histocompatibility complex (MHC) surface glycoproteins, are found in plaque and tangle lesions (Itagaki, S., McGeer, P. L., Akiyama, H. Presence of T-cytotoxic suppressor and leucocyte common antigen positive cells in Alzheimer's Disease brain tissue. Neurosci. Lett. 1988; 91: 259-264; Rogers, J., Luber-Narod, J., Styren, S. D., Civin, W. H. Expression of immune system-associated antigen by cells of the human central nervous system. Relationship to the pathology of Alzheimer's Disease. Neurobiol. Aging, 1988; 9: 330-349; McGeer, P. L., Akiyama, H., Itagaki, S., McGeer, E. G. Immune system response in Alzheimer's Disease. Can. J. Neurol. Sci. 1989; 16: 516-527; McGeer, P. L., Akiyama, H., Itagaki, S., McGeer, E. G. Activation of the classical complement pathway in brain tissue of Alzheimer patients. Neurosci. Lett. 1989; 107: 341-346; McGeer, P. L., McGeer, E. G., Rogers, J., Sibley, J. Anti-inflammatory drugs and Alzheimer's Disease. Lancet 1990; 335: 1037). Cell membranes of reactive microglia are densely occupied by complement receptors, and degenerating elements are stained by antibodies to complement proteins. Cell lysis and opsonization of debris seems to be taking place (McGeer et al., Immune system response in Alzheimer's disease; McGeer et al., Activation of the classical complement pathway in brain tissue of Alzheimer patients). Long-term anti-inflammatory chemical therapy might therefore retard the development of Alzheimer disease. One test of this hypothesis is to compare the prevalence of Alzheimer disease in the general population with the prevalence in patients with rheumatoid arthritis (RA), since such patients generally receive anti-inflammatory therapy and often contract arthritis well before the age of risk for Alzheimer disease (McGeer et al., Anti-inflammatory drugs and Alzheimer's disease).

EXAMPLE

The applicants have examined four types of prevalence data as set out in Table 1 below: rheumatoid arthritis in Alzheimer disease cases coming to necropsy, Alzheimer disease in rheumatoid arthritis clinic patients, rheumatoid arthritis in Alzheimer disease clinic patients, and rheumatoid arthritis coincident with Alzheimer disease in separation data for general hospitals.

TABLE 1

| Patients Over Age 64 with Diagnosis of Rheumatoid Arthritis and Alzheimer Disease | | | |
|---|---|---|---|
| Data Source | RA | AD | Both |
| Necropsy | | | |

TABLE 1-continued

| Patients Over Age 64 with Diagnosis of Rheumatoid Arthritis and Alzheimer Disease | | | |
|---|---|---|---|
| Data Source | RA | AD | Both |
| B.C. | — | 107 | 2 |
| Arizona | — | 62 | 0 |
| RA Clinics | | | |
| Saskatchewan | 815 | — | 4 |
| Arizona | 105 | — | 0 |
| AD Clinics | | | |
| B.C. | — | 317 | 1 |
| Arizona | — | 92 | 1 |
| General Hospitals | | | |
| B.C. | 2261 | 1960 | 16 |
| Ontario | 3987 | 3073 | 12 |
| Alberta | 375 | 30 | 0 |
| Arizona | 867 | 693 | 1 |
| Total | (7490) | (5757) | (29) |

Necropsy Data

In the records of 169 consecutive necropsy cases of dementia with some evidence of plaque and tangle lesions we found only two with an antecedent history of RA, and in neither were the necropsy findings typical of AD.

RA Clinic Data

We next reviewed data from RA clinics where patients had been followed-up regularly for a long time. Of 923 patients over 64, only four had clinical signs of AD; all four are still living so AD has not been confirmed.

AD Clinic Data

Of 409 patients with clinically diagnosed AD, only two had RA; one had acquired RA concomitantly with AD while the other was one of the atypical necropsy cases noted above.

Separation Statistics

We examined data on patients over the age of 64 who were in general hospitals with diagnoses of AD, RA or both. 0.39% of those with a diagnosis of RA were recorded as having AD, and 0.50% of those with probable AD had RA, the double diagnosis affecting 29 patients.

The prevalences found in the RA clinic and general hospital populations (see Table 1) are dramatically lower than the 2.5-10.3% reported for the over 64 North American population. Epidemiological data on RA are less well documented but a prevalence of at least 2% is likely for the age group we have been studying, and the prevalence we found in AD populations is therefore significantly less than expected.

Four possible interpretations of the observed low prevalence of coexisting AD and RA can be postulated:

(1) The reported prevalences for both AD and RA diseases in the general population are several times too high (but this seems unlikely).

(2) Only a small minority of patients having coexisting diseases were diagnosed as such. Since AD and RA have prominent symptoms, this interpretation seems unlikely, at least for the clinic populations.

(3) AD develops less often in the RA population, but this is unrelated to the long term administration of anti-inflammatory drugs. (This postulation seems unlikely.)

(4) Anti-inflammatory drug therapy confers some protection against the occurrence of AD. A detailed review of the charts of all 23 patients in British Columbia and Saskatchewan who had both diseases revealed six cases with onset of dementia at ages 62, 66, 79, 86, 93 and 96, many years after discontinuing anti-inflammatory medications; one case of RA after the onset of dementia; one case with no history of anti-inflammatory treatment and development of both diseases at age 79; seven cases without clear records; and seven cases on long-term anti-inflammatory treatment.

The above data suggest that the prevalence of Alzheimer disease in patients with rheumatoid arthritis being treated by anti-inflammatory drugs is dramatically lower than in the age-matched general population and that anti-inflammatory medication is the probable reason.

Figure 2:
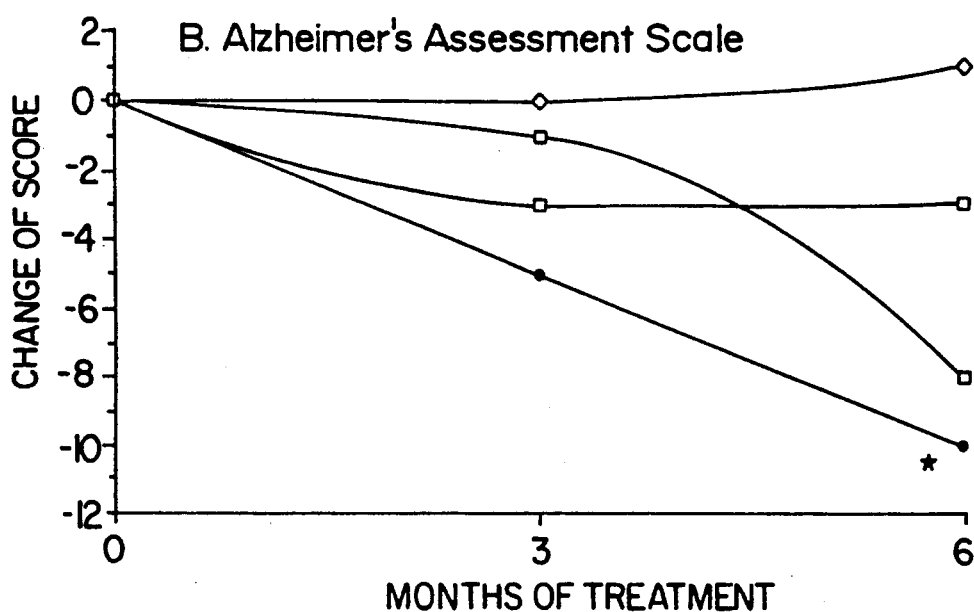
FIG. 2 illustrates a graphical depiction of Alzheimer's Assessment Scale test results plotted by change of score against months of treatment.
Figure 3:
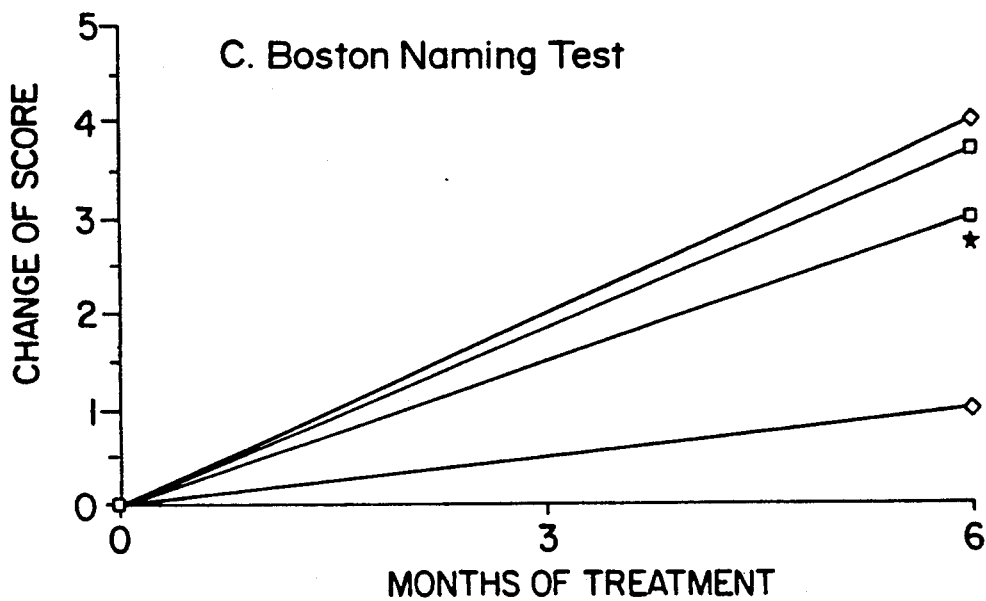
FIG. 3 illustrates a graphical depiction of Boston Naming Test test results plotted by change of score against months of treatment.
Figure 4:
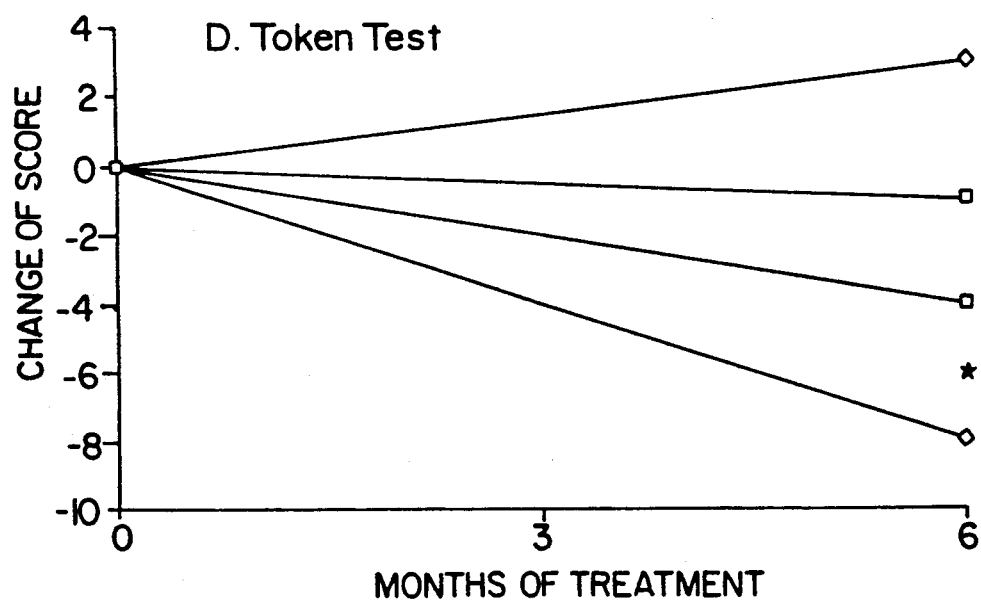
FIG. 4 illustrates a graphical depiction of Token Test test results plotted by change of score against months of treatment.

To test further the validity of this theory, we selected one NSAID, indomethacin, and administered it to a group of five clinically diagnosed early Alzheimer cases in an open, six month trial. All had been diagnosed as having AD and all were re-evaluated and the AD diagnosis confirmed by two board certified neurologists immediately before the drug trials began. Patients received four neuropsychological tests before drug administration: the Mini Mental Status Exam (FIG. 1), the Alzheimer Disease Assessment Scale (FIG. 2), the Boston Naming Test (FIG. 3), and the Token Test (FIG. 4). Neuropsychologists were blind to patient drug treatment throughout. The five patients received indomethacin according to the following regimen: 50 mg/day for week one, 100 mg/day for week two, 150 mg/day for the remainder of the six month trial. Indomethacin was administered daily in three divided doses. One patient was living independently and could not remember to take her medicine. She was removed from the study after one month on the drug. Another patient developed gastrointestinal bleeding after five months on the drug; indomethacin was withdrawn but her test scores at baseline, three months and six months are included in the analysis. The Mini Mental Status Exam and the Alzheimer Disease Assessment Scale (ADAS) were repeated at three months and six months. The Boston Naming Test and Token Test were repeated at six months only. Scores plotted on the graphs (FIGS. 1, 2, 3 and 4) are differences from baseline measures, with improvement always showing as upward lines and decrements as downward lines.

The data for the group show almost no change on the Mini Mental Status Exam, a slight improvement on the boston Naming Test, and slight decrements on the Alzheimer Assessment Scale and the Token Test. Without treatment, significant declines would have been anticipated in all of these tests over a period of six months.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of treating dementia in a human being in need thereof which comprises administering to said human being on a daily basis a sufficient amount of a non-steroidal anti-inflammatory drug to inhibit prostoglandin synthesis in vivo but insufficient to induce unwanted side effects in said human.

2. A method as claimed in claim 1 wherein the drug is selected from the group consisting of derivatives of arylcarboxylic acids, arylalkanoic acids and enolic acids, and therapeutically acceptable salts thereof.

3. A method as claimed in claim 2 wherein the arylcarboxylic acid is a salicylic acid or an anthranilic acid derivative; the arylalkanoic acid is arylacetic, arylpropionic, heteroarylacetic, indoleacetic or indeneacetic acid; and the enolic acid is pyrazolidinedione or oxicam, and therapeutically acceptable salts thereof.

4. A method of treating dementia in a human being in need thereof which comprises administering to said human being a therapeutic amount of a non-steroidal anti-inflammatory substance selected from the group consisting of salicylic acid, acetylsalicylic acid, diflunisal, choline magnesium trisalicylate, salicylate, benorylate, flufenamic acid, mefenamic acid, meclofenamic acid, niflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam and sudoxicam.

5. A method as claimed in claim 4 wherein the daily dosage is from 10 mg to 3 g of substance per 100 kg of body weight of the human being.

6. A method of treating dementia in a human being in need thereof which comprises administering to said human being a daily dosage of from about 50 mg to about 300 mg of indomethacin per 100 kg of body weight of said human being.

* * * * *